United States Patent
Taarning et al.

(10) Patent No.: US 11,040,934 B2
(45) Date of Patent: *Jun. 22, 2021

(54) PREPARATION OF 2,5,6-TRIHYDROXY-3-HEXENOIC ACID AND 2,5-DIHYDROXY-3-PENTENOIC ACID AND ESTERS THEREOF FROM C6 AND C5 SUGARS

(71) Applicant: HALDOR TOPSØE A/S, Kgs. Lyngby (DK)

(72) Inventors: Esben Taarning, Frederiksberg (DK); Irantzu Sadaba Zubiri, Frederiksberg (DK); Sebastian Meier, Værløse (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/394,009

(22) Filed: Apr. 25, 2019

(65) Prior Publication Data

US 2019/0248728 A1 Aug. 15, 2019

Related U.S. Application Data

(63) Continuation of application No. 15/737,395, filed as application No. PCT/EP2016/064186 on Jun. 20, 2016, now Pat. No. 10,315,979.

(30) Foreign Application Priority Data

Jun. 18, 2015 (EP) ..................................... 15172679
Nov. 27, 2015 (DK) ........................... PA 2015 00756
Feb. 12, 2016 (DK) ........................... PA 2016 00089
Apr. 25, 2016 (DK) ........................... PA 2016 00240

(51) Int. Cl.
| | | |
|---|---|---|
| *C07C 59/42* | (2006.01) | |
| *C07C 67/39* | (2006.01) | |
| *C07C 51/16* | (2006.01) | |
| *B01J 29/70* | (2006.01) | |
| *C07C 69/732* | (2006.01) | |

(52) U.S. Cl.
CPC ............ *C07C 59/42* (2013.01); *B01J 29/7049* (2013.01); *C07C 51/16* (2013.01); *C07C 67/39* (2013.01); *C07C 69/732* (2013.01); *C07C 2529/70* (2013.01)

(58) Field of Classification Search
CPC ......... C07C 51/16; C07C 59/42; C07C 67/39; C07C 69/732; C07C 2529/70; C07C 51/00; C07C 51/43; C07C 51/44; C07C 51/50; C07C 67/52; C07C 67/54; C07C 67/62; B01J 29/7049; B01J 29/7057

See application file for complete search history.

(56) References Cited

U.S. PATENT DOCUMENTS

| | | |
|---|---|---|
| 6,306,364 B1 | 10/2001 | Valencia et al. |
| 2015/0045576 A1 | 2/2015 | Benecke et al. |

FOREIGN PATENT DOCUMENTS

| | | | |
|---|---|---|---|
| EP | 2 184 270 B1 | | 2/2013 |
| WO | 2015/024875 A1 | | 2/2015 |
| WO | WO2015/024875 | * | 2/2015 |

OTHER PUBLICATIONS

International Search Report (PCT/ISA/210) dated Aug. 19, 2016, by the European Patent Office as the International Searching Authority for International Application No. PCT/EP2016/064186.
Written Opinion (PCT/ISA/237) dated Aug. 19, 2016, by the Japanese Patent Office as the International Searching Authority for International Application No. PCT/EP2016/064186.
International Preliminary Report on Patentability (PCT/IPEA/409) dated Aug. 28, 2017, by the European Patent Office as the International Preliminary Examining Authority for International Application No. PCT/EP2016/064186.
Holm et al., "Sn-Beta catalysed conversion of hemicellulosic sugars", Green Chem., Jan. 2012, pp. 702-706, vol. 14, No. 3.
Löwendahl et al., "Nonoxidative and oxidative alkaline degradation of mannan", Acte Chemica Scandinavica B, Jan. 1980, pp. 623-628, vol. 34.
Tolborg et al., "Tin-containing Silicates: Alkali Salts Improve Methyl Lactate Yield from Sugars", ChemSusChem, 2015, pp. 613-617, vol. 8.
Holm, et al., "Conversion of Sugars to Lactic Acid Derivatives Using Heterogeneous Zeotype Catalysts", Science, Apr. 2010, 602-605.
Johansson, et al., "Endwise Degradation of Hydrocellulose in Bicarbonate Solution", Journal of Applied Polymer Science, 1978, 615-623.
Löwendahl, et al., "Influence of iron and cobalt compounds upon oxygen-alkali treatment of cellulose", Svensk Papperstidning, 1974, 593-602.
Yang, et al., "Alkaline degradation of fructofuranosides", Carbohydrate Research, 1996, 47-57.
White et al (Basic Energy Sciences Advisory Committee Subpanel Workshop Report, Opportunities for Catalysis in the 21st Century, 2002 (Year: 2002).

* cited by examiner

*Primary Examiner* — Yevgeny Valenrod
*Assistant Examiner* — Blaine G Doletski
(74) *Attorney, Agent, or Firm* — Buchanan Ingersoll & Rooney P.C.

(57) ABSTRACT

Preparation of 2,5,6-trihydroxy-3-hexenoic acid and 2,5-dihydroxy-3-pentenoic acid and esters thereof from C6 and C5 sugars in the presence of a Lewis Acid material, wherein the yield of the 2,5,6-trihydroxy-3-hexenoic acid or 2,5-dihydroxy-3-pentenoic acid or esters thereof exceeds 15%. The process including the steps of contacting a saccharide composition including one or more C6 and/or C5 saccharide units with a Lewis Acid material; and recovering 2,5,6-trihydroxy-3-hexenoic acid and/or 2,5-dihydroxy-3-pentenoic acid or the esters thereof.

20 Claims, No Drawings

PREPARATION OF 2,5,6-TRIHYDROXY-3-HEXENOIC ACID AND 2,5-DIHYDROXY-3-PENTENOIC ACID AND ESTERS THEREOF FROM C6 AND C5 SUGARS

CROSS REFERENCE TO RELATED APPLICATIONS

The present application is a continuation of U.S. application Ser. No. 15/737,395, filed on Dec. 18, 2017, which is a U.S. national stage of International Application No. PCT/EP2016/064186, filed on Jun. 20, 2016, which claims the benefit of Danish Application No. PA 2016 00240, filed on Apr. 25, 2016, the benefit of Danish Application No. PA 2016 00089, filed on Feb. 12, 2016, the benefit of Danish Application No. PA 2015 00756, filed on Nov. 27, 2015, and the benefit of European Application No. 15172679.1, filed on Jun. 18, 2015. The entire contents of each of U.S. application Ser. No. 15/737,395, International Application No. PCT/EP2016/064186, Danish Application No. PA 2016 00240, Danish Application No. PA 2016 00089, Danish Application No. PA 2015 00756, and European Application No. 15172679.1 are hereby incorporated herein by reference in their entirety.

DESCRIPTION

The present invention relates to the preparation and recovery of 2,5,6-trihydroxy-3-hexenoic acid and 2,5-dihydroxy-3-pentenoic acid and esters thereof from C6 and C5 sugars in the presence of a Lewis acid catalyst.

BACKGROUND

Carbohydrates represent the largest fraction of biomass, and various strategies for their efficient use as a feedstock for the preparation of commercial chemicals are being established. Biomass is of particular interest due to its potential as supplementing, and ultimately replacing petroleum as a feedstock for such purposes. Carbohydrates obtainable from biomass comprise C6 and C5 sugars and are of particular industrial interest as they are a potential source of highly functionalized short chain carbon compounds. This is of particular importance for highly functionalized short chain carbon compounds that are commercially unavailable, such as 2,5,6-trihydroxy-3-hexenoic acid and 2,5-dihydroxy-3-pentenoic acid and esters thereof. A general way to denominate these compounds is alpha-hydroxy-beta-ene-acids and esters thereof. The general molecular structure of such compounds is

R'—HC=CH—CHOH—COOR    (I)

where R' and R represent —H,-alkyl or hydroxyalkyl groups.

Currently, 2,5,6-trihydroxy-3-hexenoic acid and 2,5-dihydroxy-3-pentenoic acid are prepared by alkaline degradation of cellulose: Svensk Papperstidning (1974) 16, p 593-602 and J. Appl. Polymer Sci. (1978) 22, pp 615-623; and mannan: Acta Chem Scan. (1980) 40, pp 9-14. However, the product compositions of these reactions comprise numerous compounds, and therefore the products obtained are in low yields (5 mg per g of product). Additionally, the methods proposed are not industrially feasible due to the variety of reaction products produced in the process.

It is known that sugar compositions comprising C6 and/or C5 sugars may be substrates in the preparation of methyl lactate in the presence of Sn-BEA. EP 2 184 270 B1 and Science (2010) 328, pp 602-605 report yields of methyl lactate of 64%, 43% and 44% at 160° C. in methanol from sucrose, glucose and fructose, respectively. Numerous by-products are, however, observed in connection with this reaction, and the major by-product reported is methyl vinylglycolate (3-11%).

It has been suggested that small amounts of compounds similar to saccharinic acids, including a noticeable amount of highly polar products may be produced during the disclosed reaction. It has been postulated that these highly polar products are methyl esters of C6 saccharinic acids. Such C6 saccharinic acids are described in Carbohydrate Res. (1996) 280, pp 47-57. However, this reference is silent with regard to the identity, the amount in percentage yield and the number of compounds that are components of the highly polar products.

Green Chem. (2012) 14, pp 702-706 discloses similar reaction conditions to Science (2010) 328, pp 602-605, wherein the temperature of the reaction is varied. The combined yields of identified products and unconverted sugars are at least 51%.

ChemSusChem (2015) 8, pp 613-617 discloses an increase in methyl lactate yield (from 20-25% to 66-71%) obtained from sugars in the presence of a heterogeneous stannosilicate catalyst when an alkali ion is added to the reaction process.

Accordingly, it is desirable to provide a Lewis acid based catalytic processes for the preparation of highly functionalized C6 and C5 compounds. Additionally, it is desirable to provide highly functionalized C6 and C5 compounds in high yields by way of industrially applicable, direct, selective processes.

DESCRIPTION

According to the present invention it has been discovered that upon selection of specific reaction conditions, such as concentration of sugar in the sugar composition, amount of catalyst, solvent and alkalinity of the medium, it is possible selectively and in high yields to obtain alpha-hydroxy-beta-ene-acids, such as 2,5,6-trihydroxy-3-hexenoic acid and 2,5-dihydroxy-3-pentenoic acid and esters thereof from sugar compositions comprising one or more sugars selected from the group consisting of C6 and C5 sugars.

According to the present invention a process is provided for the preparation of alpha-hydroxy-beta-ene-acids or esters thereof of the formula

R'—HC=CH—CHOH—COOR    (I)

wherein

R is selected from the group consisting of —H and $C_1$-$C_8$-alkyl; and

R' is hydroxymethyl or 1,2-dihydroxyethyl;

the process comprising the steps of:
a. contacting a saccharide composition comprising one or more C6 and/or C5 saccharide units with a Lewis Acid material; and
b. recovering 2,5,6-trihydroxy-3-hexenoic acid and/or 2,5-dihydroxy-3-pentenoic acid or the esters thereof.

An advantage of this process is that the 2,5,6-trihydroxy-3-hexenoic acid or 2,5-dihydroxy-3-pentenoic acid and esters thereof can be recovered in yields above 15%. Preferably, the yield of esters is higher than 20%, 25%, 30%.

According to an embodiment of the present invention, the $C_1$-$C_8$-alkyl is selected from the group consisting of methyl-, ethyl-, propyl-, iso-propyl-, butyl-, isobutyl-, pentyl-, hexyl-, heptyl-, octyl-.

Such alpha-hydroxy-beta-ene-acids or esters thereof are highly functionalized, and as platform molecules (or base chemical/intermediate) they present advantageous characteristics for the chemical industry such as for producing polyesters. They may be polymerized or copolymerized with other monomers such as e.g. lactic acid or ε-caprolactone.

The compounds of formula (I) are structurally interesting molecule for which many applications can be envisioned. The structure of the compound resembles the structure of 6-hydroxycaproic acid, and therefore the compound of formula I can be utilized in similar applications. However, unlike 6-hydroxycaproic acid, the compound of the formula (I) allows other functionalities, such as a double bond and a secondary alcohol, which introduces the possibility of using it as a functionalized polyester monomer.

The esters of 2,5,6-trihydroxy-3-hexenoic acid or 2,5-dihydroxy-3-pentenoic acid are preferably methyl esters. 2,5,6-trihydroxy-3-hexenoic acid methyl ester and 2,5-dihydroxy-3-pentenoic acid methyl ester may also be known as 'THM' and 'DPM'.

Where nothing else is indicated, the yield of the 2,5,6-trihydroxy-3-hexenoic acid or 2,5-dihydroxy-3-pentenoic acid and esters thereof is calculated on a molar basis based on the sugar starting material.

The saccharide composition may also be referred to as a "sugar composition" or "substrate". In the present context, a saccharide composition is meant to refer to a saccharide or sugar dissolved in a solvent. Similarly in the present context, the terms "saccharide", "sugar" and "substrate" are used interchangeably. The saccharide composition comprises preferably one or more C6 and/or C5 saccharide units selected from the group consisting of sucrose, xylose, arabinose, mannose, tagatose, galactose, glucose, fructose, inulin, amylopectin (starch) and sugar syrup. Examples of the use of various saccharide compositions can be found in Table 6.

According to an embodiment of the invention, the concentration of C6 and/or C5 compounds (saccharide units) in the sugar composition (saccharide composition) is higher than 10 g/L, preferably higher than 50 g/L. In the present context, the "concentration of C6 and/or C5 compounds" is meant to refer to the total or combined concentration of the saccharide monomers in the saccharide composition.

Lewis Acid materials act as an electron pair acceptor to increase the reactivity of a substrate. In the present context, the Lewis Acid materials catalyze the conversion of saccharide units (sugars) into e.g. 2,5,6-trihydroxy-3-hexenoic acid and 2,5-dihydroxy-3-pentenoic acid and the esters thereof. The Lewis acid materials include tin salts, such as tin chloride (SnCl4 and SnCl2), tin fluoride (SnF4 and SnF2), tin bromide (SnBr4 and SnBr2), tin iodide (SnI4 and SnI2), tin acetylacetonate (SnC10H14O4), tin pyrophosphate (Sn2P2O7), tin acetate (Sn(CH3CO2)4 and Sn(CH3CO2)2), tin oxalate (Sn(C2O4)2 and SnC2O4), tin triflate ((CF3SO3)2Sn and CF(3SO3)4Sn)) as well as materials presenting a porous structure, such as solid Lewis Acids. In the present context, the Lewis Acid materials may also be referred to as "catalysts".

Solid Lewis Acid materials may be crystalline or non-crystalline. Non-crystalline solid Lewis Acid materials include ordered mesoporous amorphous materials, such as Sn-MCM-41 and Sn-SBA-15, or other mesoporous amorphous forms. Crystalline microporous material includes zeolite materials and zeotype materials. It can be advantageous to occasionally regenerate the Lewis Acid materials e.g. by calcining the materials at a temperature above 400° C. in order to maintain a high selectivity and/or a yield of 2,5,6-trihydroxy-3-hexenoic acid and 2,5-dihydroxy-3-pentenoic acid and the esters thereof.

Zeolite materials are crystalline alumino-silicates of a microporous crystalline structure.

A zeotype material is a material where the aluminum atoms of a zeolite material are partly or fully substituted by a metal (metal atoms), such as zirconium (Zr), titanium (Ti) and tin (Sn).

The present invention relates to a process wherein the Lewis acid material framework structure is selected from the group consisting of BEA, MFI, FAU, MOR, FER, MWW, MCM-41 and SBA-15, or mixtures thereof.

The present invention relates to a process wherein the Lewis acid material comprises an active metal selected from one or more of the groups consisting of Sn, Ti, Pb, Zr, Ge and Hf or mixtures thereof.

The present invention relates to a process wherein the Lewis acid material is selected from the group consisting of Sn-BEA, Sn-MFI, Sn-FAU, Sn-MOR, Sn-MWW, Sn-MCM-41 and Sn-SBA-15, SnCl$_4$, SnCl$_2$ or mixtures thereof. Preferably, the material is Sn-BEA or Sn-MCM-41 or SnCl$_4$.

According to a further embodiment of the invention, the Sn-BEA is prepared by a direct synthesis process using hydrogen fluoride or by a post treatment process as collected in Table 2 and Table 7. Examples of direct synthesis processes are described in EP 1 010 667 B1. The Sn-BEA is prepared by a fluoride direct synthesis process or by a post treatment process in order to avoid the presence of alkaline components in the Sn-BEA, Such alkaline components are, for example: potassium ions as illustrated in WO2015/024875 A1. Preferably, any alkaline material present in the reaction solution is present in a concentration of less than 0.13 mM or in an amount of less than 0.5 wt % of the catalyst composition.

An example of a post treatment process for the preparation of Sn-BEA is illustrated in WO2015/024875 A1 (Catalyst A). The hydrogen fluoride route (also known as the direct synthesis process), is described in EP 1 010 667 B1.

The process according to the present invention may be conducted as a continuous flow process or a batch process. In the present context, a continuous flow process is to be understood as a reaction or process that occurs over a prolonged period of time, and the reactant is fed through a reaction chamber in a solvent. It is an advantage of a continuous flow process that it is suitable for large scale production.

According to a further embodiment of the invention, the process is a continuous process, wherein the weight hourly space velocity is between 0.005 and 10 h-1, such as from 0.01 to 5 h-1, or 0.05 to 1 h-1

According to a further embodiment of the invention, the ratio of the catalyst to substrate is optimized for each saccharide concentration as shown in Table 4 to obtain a yield of 2,5,6-trihydroxy-3-hexenoic acid or 2,5-dihydroxy-3-pentenoic acid and esters thereof is higher than 15%, 20%, 25%, 30%, 35% or even as high as 50%. For example the mass ratio ($R_m$) of catalyst to substrate is preferably $R_m$>0.1, such as 0.2, more preferred within the range of from $0.1 < R_m < 0.8$, such as $0.25 < R_m < 0.75$ when the saccharide is xylose.

According to a further aspect of the invention, the process is carried out at a temperature from 110° C. to 200° C., from 110° C. to 190° C., from 110 to 180° C., preferably at a temperature from 140 to 170° C., as shown in Table 1.

According to another aspect of the invention, the solvent is a polar solvent. A polar solvent is meant to refer to a composition having a dielectric constant exceeding 15 such as DMSO, dimethylformamide, acetonitrile, methanol, ethanol, water or mixtures thereof. An advantage of using polar or slightly polar solvents is that the yields of 2,5,6-trihydroxy-3-hexenoic acid or 2,5-dihydroxy-3-pentenoic acid and esters thereof can be above 20%. Preferably, the yield of esters is higher than 25%, 30%, 35%, 40%, 45% or even as high as 50% based on moles of initial saccharide.

According to an embodiment of the invention, the solvent comprises DMSO. Surprisingly, the yield of 2,5,6-trihydroxy-3-hexenoic acid (THA) and/or 2,5-dihydroxy-3-pentenoic acid (DPA) is above 20%, such as above 25, 30, 35, 40 or 45% as shown in Table 8. Preferably, the solvent comprises DMSO and water, wherein the concentration of water is within the range of from 2 to 50 wt %, such as from 5 to 30%. Preferably, the solvent is a mixture of DMSO and water.

According to the present invention, the concentration of alkali metal ions present in the reaction solution or in the environment of the Lewis Acid material is kept at a concentration of less than 0.13 mM or an amount of less than 0.5 wt % of the catalyst composition.

An advantage of keeping the concentration of ions low is that yields 2,5,6-trihydroxy-3-hexenoic acid or 2,5-dihydroxy-3-pentenoic acid and esters thereof above 15% may be obtained, as shown in Table 5. Preferably the yield of esters is higher than 20%, 25%, 30%, 35%, 40%, 45% or even as high as 50%. When the concentration of alkali metal ion present is less than 0.13 mM, the yield of methyl lactate is kept below 30%, more preferably below 20% or 15% with the result that an increased conversion rate of saccharides into the desired products of Formula I is obtained.

As used herein, an alkali metal ion is to be understood as a metal ion originating from either the element itself or the salt of an alkali metal. More specifically, the salt of the alkali metal comprises at least one metal ion and at least one anion. Examples of metal ion are potassium, sodium, lithium, rubidium and caesium. Examples of a salt of the alkali metal are carbonate, nitrate, acetate, lactate, chloride, bromide and hydroxide. Examples of salts are $K_2CO_3$, $KNO_3$, KCl, potassium acetate ($CH_3CO_2K$), potassium lactate ($CH_3CH(OH)CO_2K$), $Na_2CO_3$, $Li_2CO_3$, $Rb_2CO_3$.

Also according to the present invention, the concentration of the compounds of formula I, such as 2,5,6-trihydroxy-3-hexenoic acid or 2,5-dihydroxy-3-pentenoic acid and/or esters thereof in the reaction medium is higher than 10 g/L, with a yield exceeding 15%, 20%, 25%, 30%, 35% or even as high as 50%. Also according to the present invention, the concentration of saccharide in the reaction composition is higher than 5 wt %, as shown in Table 3.

EXAMPLES

Preparation of Sn-BEA

A. Process for the Preparation of Sn-BEA Via a Direct Synthesis Method (HF Route).

Sn-Beta zeolites were synthesized by modifying the route described by Valencia et al. [U.S. Pat. No. 6,306,364 B1] In a typical synthesis procedure, 30.6 g f tetraethyl orthosilicate (TEOS, Aldrich, 98%) was added to 33.1 g of tetraethylammonium hydroxide (TEAOH, Sigma-Aldrich, 35% in water) under careful stirring and forming a two-phase solution. After stirring for ~60 min, one phase is obtained and tin(IV) chloride pentahydrate ($SnCl_4.5H_2O$, Aldrich, 98%) dissolved in 2.0 mL of demineralized water was added drop wise. Stirring was maintained for several hours to allow ethanol formed from the hydrolysis of TEOS to evaporate. Finally, 3.1 g hydrofluoric acid (HF, Fluka, 47-51%) in 1.6 g of demineralized water was added to the gel, yielding a solid with the molar composition; $1.0Si:0.005Sn:0.02Cl^-:0.55TEA^+:0.55F:7.5H_2O$. All samples were then homogenized and transferred to a Teflon-container placed in a stainless steel autoclave and subsequently placed at 140° C. for 14 days. The solid was recovered by filtration and washed with demineralized water, followed by drying overnight at 80° C. in air. The organic template contained within the material was removed by heating the sample at 2° C./min to 550° C. in static air, and this temperature was maintained for 6 h.

B. Process of Preparing Sn-BEA Via a Post-Treatment Method.

Sn/Beta (Si/Sn=125) was prepared according to the procedure described in ChemSusChem 2015, 8, 613-617. Commercial zeolite Beta, viz. (Zeolyst, Si/Al 12.5, $NH_4^+$ form) is calcined at 550° C. for 6 h to obtain the $H^+$ form and treated with 10 g of concentrated nitric acid ($HNO_3$, Sigma-Aldrich, ≥65%) per gram of zeolite Beta powder for 12 h at 80° C. The resulting solid is filtered, washed with ample water and calcined at 550° C. for 6 h using a ramp of 2° C./min to obtain the dealuminated Beta. This solid is impregnated by incipient wetness methodology with a Si/Sn ratio of 125. For this purpose, tin(II) chloride (0.128 g, Sigma-Aldrich, 98%) is dissolved in 5.75 mL water and added to the dealuminated 5 g of Beta. After the impregnation process, the samples are dried 12 h at 110° C. and calcined again at 550° C. for 6 h.

C. Process of Preparing Sn-MCM-41

The ordered mesoporous stannosilicate, Sn-MCM-41, was prepared according to the route described in Green Chemistry, 2011, 13, 1175-1181. In a typical synthesis, 26.4 g of tetraethylammonium silicate (TMAS, Aldrich, 15-20 wt % in water, ≥99.99%) was slowly added to a solution of 13.0 g of hexadecyltrimethylammonium bromide (CTABr, Sigma, ≥99.0%) dissolved in 38.0 g of water, and the mixture was allowed to stir for approx. 1 hour. At this point, $SnCl_4.5H_2O$ and hydrochloric acid (HCl, Sigma-Aldrich, min. 37%) in 2.1 g of water were added dropwise to the solution and allowed to stir for 1.5 h. To this solution 12.2 g of TEOS was added and stirred for 3 h, leading to a gel composition of $1.0Si:0.005Sn:0.44CTABn0.27TMA:0.08Cl^-:46H_2O$. The samples were then transferred to a Teflon-lined container placed in a stainless steel autoclave and placed in a pre-heated oven at 140° C. for 15 h. The solid was recovered by filtration, washed with ample water and then dried overnight at 80° C. The material was finalized by calcination, where the sample was heated to 550° C. at 2° C./min in static air and maintaining this temperature for 6 h.

Example 1 a. In a typical reaction, 0.150 g of alkali-free Sn-Beta zeolite (Si/Sn=150), 0.45 g of sugar and 15.0 g of anhydrous methanol (15.0 g, Sigma-Aldrich, >99.8%) is added to a stainless steel pressure vessel (40 cc, Swagelok). The reactor is closed and placed in a preheated oil bath at 160° C. under stirring at 700 rpm and allowed to react for 20 hours. After reaction the vessel is rapidly cooled by submerging the reactor in cold water. The sugar derivative was identified by GC-MS (Agilent 6890 with a Phenomenex Zebron ZB-5 column equipped with an Agilent 5973 mass selective detector).

b. Alternatively, 4.0 g of anhydrous methanol (Sigma-Aldrich, >99.8%), 0.36 g sugar (Sigma-Aldrich, >99%) and the desired amount of alkali-free Sn-Beta were added to a 5 mL glass microwave vial (Biotage). The reaction vessel was heated to 160° C. while stirred at 600 rpm for 2 hours in a Biotage Initiator+ microwave synthesizer. After cooling, samples were filtered and subsequently analyzed. In relevant reactions, alkali salt was added by replacing the appropriate portion of the methanol solvent with a 1 mM standard solution of K2CO3 (Sigma-Aldrich, 99.0%) in methanol to obtain the required concentration.

Anhydrous tin(IV) chloride (Sigma Aldrich, St. Louis, Mo., USA) was dissolved in d6-DMSO (Sigma Aldrich) to a final concentration of 10% (w/v). Carbohydrates including glucose, fructose, ribose, arabinose, inulin, xylan and amylopectin (starch) (all from Sigma Aldrich, Megazymes (Bray, Ireland) Carbosynth (Compton, UK)) were dissolved in d6-DMSO at concentrations corresponding to 0.3-1 M saccharide monomer (30-100 mg/500 µl final volume) in 1.5 ml Eppendorf safelock tubes. Water (D2O) was added to a final volume ratio (v/v) of 0, 5, 10, 15 or 20%. Anhydrous tin(IV) chloride was added from the stock solution, typically to a final carbohydrate:catalyst molar ratio of 10:1. Reaction mixtures containing carbohydrate in d6-DMSO with 10-vol % catalyst and defined water fraction were incubated while shaking at 600 rpm at 99° C. for 20 hours in an Eppendorf Thermomixer. Samples were transferred to 5 mm NMR sample tubes after the reaction and immediately analyzed at 30° C. by 1H and 13C NMR spectroscopy. The samples had some miscoloring due to humin formation, but remained transparent (albeit slightly colored) throughout the experiments with the best THA yields. Yields were estimated by comparing the 13C NMR signal integrals of a substrate solution with the signal integrals? of the product mixture (both normalized to the d6-DMSO signal) and by integrating the signals not overlapping the hydroxyl-region of an 1H NMR spectrum, which includes lactate and lactate oligomer methyl groups, 3-deoxy compound methylene groups and THA olefin as well as HMF furan hydrogen signals. Lactate molar fractions were divided by a factor of two when deriving the yields as % molC from C6 sugars. In situ experiments were performed by transferring the reaction mixtures from the 1.5 ml Eppendorf safelock tubes directly to NMR tubes followed by heating the NMR tubes in the spectrometer to the desired temperature. The reaction progress was then followed by pseudo-2D spectra containing series of 1H or 13C NMR spectra. For signal identification, homo- and heteronuclear assignment spectra were recorded for glucose- and xylose derived? reaction mixtures. All spectra were recorded on a Bruker (Fallanden, Switzerland) Avance II 800 MHz spectrometer equipped with a TCI Z-gradient CryoProbe and an 18.7 T magnet (Oxford Magnet Technology, Oxford, U.K.) or on a Bruker Avance III 600 MHz spectrometer equipped with a room temperature smart probe. NMR spectra were recorded, processed and analyzed with Bruker Topspin 2.1 or Bruker Topspin 3.0.

Examples 2-3

Example 1b was followed where the temperature of the process was increased to 170° C. and decreased to 14° C., respectively. The catalyst used is Sn-Beta (Si/Sn=150) according to method A.

TABLE 1

Yield of 2,5,6-trihydroxy-3-hexenoic acid methyl ester (THM) from a C6 sugar (glucose) at varying process temperatures.

| Example | Temperature (° C.) | Yield (%) |
|---|---|---|
| 1 | 140 | 12 |
| 2 | 160 | 14.5 |
| 3 | 170 | 17.3 |

As seen in Table 1, increasing the temperature provides increasing yields.

Examples 4-6

Example 1a was followed where the starting material was xylose instead of glucose at 160° C., and different catalysts were used.

TABLE 2

Yield of 2,5-dihydroxy-3-pentenoic acid methyl ester (DPM) from a C5 sugar (xylose) with different catalysts.

| Example | Catalyst | Yield (%) |
|---|---|---|
| 4 | Method A (Si/Sn = 200) | 27.5 |
| 5 | Method A (Si/Sn = 150) | 24.5 |
| 6 | Method B (Si/Sn = 125) | 18.1 |

As seen in Table 2, method A for the preparation of the catalyst provides increased yields under the conditions given.

Examples 7-10

Example 1b was followed where the starting material was xylose at 160° C. and different initial concentrations in wt % of xylose in the reaction composition.

TABLE 3

Yield of 2,5-dihydroxy-3-pentenoic acid methyl ester (DPM) at 160° C. Catalyst used is Sn-Beta (Si/Sn = 150) according to method A.

| Example | Xylose concentration wt % | Yield DPM (%) |
|---|---|---|
| 7 | 4.3 | 26 |
| 8 | 8.3 | 32 |
| 9 | 15 | 30 |
| 10 | 23 | 30 |

As observed in Table 3, it seems that at a higher xylose concentration results in increased yields of DPM until a threshold yield of DPM is achieved at a xylose concentration of around 7 wt % and possibly with a little peak around 8-9 wt %. This fact is surprising since sugar experiments are typically conducted in concentrations below 5 g/L. It is especially interesting to note that a concentration as high as 30 g/L produces DPM in a comparable yield as the lower concentrations. It is unusual to obtain high yields of products when using high concentrations of saccharides.

Examples 11-16

Example 1b was followed where the starting material was xylose at 160° C., and different amounts of catalyst leading to different catalyst to substrate ratios were used.

TABLE 4

Yield of 2,5-dihydroxy-3-pentenoic acid methyl ester (DPM) and methyl lactate (ML), xylose concentration 9 wt %. Catalyst used is Sn-Beta (Si/Sn = 150) according to method A.

| Example | Mass ratio catalyst/substrate | DPM Yield (%) | ML Yield (%) |
|---|---|---|---|
| 11 | 0 | 0 | 1 |
| 12 | 0.125 | 15 | 25 |
| 13 | 0.25 | 23 | 24 |
| 14 | 0.5 | 32 | 15 |
| 15 | 0.75 | 30 | 15 |
| 16 | 1 | 30 | 14 |

As shown in Table 4, when the ratio of catalyst/substrate is 0.5 then the highest yield of DPM was obtained. Accordingly, the yield of DPM can be optimized by adjusting the ratio of catalyst/substrate. It is very interesting to note that the yield of ML decreased concomitantly with the increase in DPM. This change in selectivity of the catalyst when different amounts of catalyst were used is very surprising and has not been reported earlier. In order to obtain a high yield of DPM, the ratio of catalyst/substrate should be above 0.25.

Examples 17-24

Example 1b was followed where the starting material was xylose at 160° C., and different concentrations of alkali metal ion ($K_2CO_3$) in methanol were used.

TABLE 5

Yield of 2,5-dihydroxy-3-pentenoic acid methyl ester (DPM) and methyl lactate (ML), xylose concentration 9 wt %. Catalyst used is Sn-Beta (Si/Sn = 150) according to method A.

| Example | Concentration of $K_2CO_3$ in methanol (mM) | DPM Yield (%) | ML Yield (%) |
|---|---|---|---|
| 17 | 0 | 32 | 13 |
| 18 | 0.05 | 21 | 27 |
| 19 | 0.1 | 14 | 34 |
| 20 | 0.15 | 11 | 34 |
| 21 | 0.25 | 8 | 35 |
| 22 | 0.5 | 4 | 29 |
| 23 | 0.75 | 2 | 23 |
| 24 | 1 | 2 | 16 |

As seen in Table 5, the concentration of alkali metal ion has an effect on the yield of DPM. As exemplified here for the case of $K_2CO_3$, a concentration of alkali metal ion below 0.1 mM led to DPM yields above 20%. ML yield must be kept below 30%. Therefore DPM is the main product found in the reaction mixture.

Examples 25-30

Example 1a was followed where the starting materials were other sugars (instead of glucose) at 160° C. Catalyst used is Sn-Beta (Si/Sn=125) according to method B.

TABLE 6

Yield of 2,5,6-trihydroxy-3-hexenoic acid methyl ester (THM) from different sugars. Catalyst used is Sn-Beta (Si/Sn = 125) according to method B.

| Example | Sugar | Yield (%) |
|---|---|---|
| 25 | Fructose | 17.8 |
| 26 | Mannose | 14.7 |
| 27 | Sorbose | 17.3 |
| 28 | Galactose | 11.5 |
| 29 | Tagatose | 9.0 |
| 30 | Sucrose | 15.3 |

As seen in Table 6, all the tested C6 monosaccharides and disaccharides produce THM.

Examples 31-33

Example 1 was followed at 160° C. and different catalysts were used, said catalysts being prepared according to examples B and C.

TABLE 7

Yield of 2,5,6-trihydroxy-3-hexenoic acid methyl ester (THM) from different catalysts

| Example | Catalyst | Yield (%) |
|---|---|---|
| 31 | Method A (Si/Sn = 125) | 16.1 |
| 32 | Method B (Si/Sn = 125) | 13.8 |
| 33 | Method C (Si/Sn = 125) | 17.7 |

As seen in Table 7, method C for the preparation of the catalyst is preferred.

Examples 34-38

Example 1c was followed at 90° C. and different amounts of water were added in DMSO.

TABLE 8

Yield of 2,5,6-trihydroxy-3-hexenoic acid (THA) with different amounts of water

| Example | Water (wt %) | THA Yield (%) | HMF Yield (%) |
|---|---|---|---|
| 34 | 0 | 20 | 42 |
| 35 | 5 | 47 | 32 |
| 36 | 10 | 49 | 25 |
| 37 | 15 | 48 | 22 |
| 38 | 20 | 43 | 20 |

As seen in Table 8, the presence of 5-15 wt % of water in the solvent mixture is preferred.

Examples 39-44

Example 1c was followed at 90° C. and 2,5-dihydroxy-3-pentenoic acid from different sugars in DMSO.

TABLE 9

Yield of 2,5,6-trihydroxy-3-hexenoic acid (THA) and 2,5-dihydroxy-3-pentenoic acid (DPA) from different sugars

| Example | Sugar | THA Yield (%) | DPA Yield (%) |
|---|---|---|---|
| 39 | Glucose | 49 | — |
| 40 | Sucrose | 44 | — |

TABLE 9-continued

Yield of 2,5,6-trihydroxy-3-hexenoic acid (THA) and
2,5-dihydroxy-3-pentenoic acid (DPA) from different sugars

| Example | Sugar | THA Yield (%) | DPA Yield (%) |
|---|---|---|---|
| 41 | Fructose | 44 | — |
| 42 | Xylose | — | 49 |
| 43 | Arabinose | — | 48 |
| 44 | Inulin | 42 | — |

Example 45

Production, purification and identification of 2,5,6-trihydroxy-3-hexenoic acid methyl ester (THM) and 2,5-dihydroxy-3-pentenoic acid methyl ester (DPM)
Production and Purification of 2,5,6-Trihydroxy-3-Hexenoic Acid Methyl Ester (THM)

Post-treated Sn-Beta (3 g), Glucose (12 g, Sigma-Aldrich, >99.0%) and methanol (200 g, Sigma-Aldrich, >99.8%) were added to the Teflon liner of a 1 L autoclave reactor (Autoclave Engineers). The reactor was sealed and heated to 160° C. while stirred at 450 rpm for 16 hours. The reaction mixture was then cooled and filtered and resulted in the crude reaction mixture. The crude reaction mixture was concentrated under reduced pressure at 40° C. 2.1 g of the concentrate was dissolved in methanol, evaporated onto Celite and purified by flash column chromatography (silica gel 15 40 Mesh, $CH_2Cl_2$->20:1 $CH_2Cl_2$:MeOH) affording 0.30 g of pure THM.
Production and Purification of 2,5-Dihydroxy-3-Pentenoic Acid Methyl Ester (DPM)

Post-treated Sn-Beta (7.5 g), Xylose (30 g, Sigma-Aldrich, >99%), demineralized water (3 g) and methanol (300 g, Sigma-Aldrich, >99.8%) were added to the Teflon liner of a 1 L autoclave reactor (Autoclave Engineers). The reactor was sealed and heated to 160° C. while stirred at 450 rpm for 16 hours. The reaction mixture was then cooled and filtered and resulted in a crude reaction mixture including 15-20% DPM. The crude reaction mixture was concentrated under reduced pressure. The concentrate was dissolved in methanol, evaporated onto Celite and purified by dry column vacuum chromatography (silica gel 60 (15-40 µm), heptane->ethyl acetate), affording DPM of >94% purity (GC-MS).
Analysis and Identification NMR experiments were recorded on a Bruker Ascend 400 spectrometer, 1H-NMR was recorded at 400 MHz and 13C-NMR was recorded at 100 MHz. The chemical shifts are given in ppm relative to the residual solvent signals, and the chemical shifts are reported downfield to TMS. HRMS was recorded on an LC-TOF (ES).

2,5,6-trihydroxy-3-hexenoic Acid Methyl Ester (THM)

1H-NMR (400 MHz, $CD_3OD$): δ (ppm) 5.93 (dd, J=15.3, 4.3 Hz, 1H), 5.88 (dd, J=15.3, 4.1 Hz, 1H), 4.69 (d, J=4.1 Hz, 1H), 4.14 (ddd, J=6.7, 4.7, 4.1 Hz, 1H), 3.73 (s, 3H), 3.51 (dd, J=10.9, 4.7 Hz, 1H) 3.45 (dd, J=10.9, 6.7 Hz, 1H). $^{13}$C-NMR (100 MHz, CD3OD): δ (ppm) 174.6, 133.8, 129.4, 73.4, 72.2, 67.0, 52.6. HRMS (ESI+) m/z calculated for $C_7H_{12}O_5$ [M+Na]+: 199.0577; found: 199.0572.

2,5-dihydroxy-3-pentenoic Acid Methyl Ester (DPM)

$^1$H NMR (400 MHz, $CD_3OD$) δ 5.89 (dtd, J=15.5, 5.0, 1.4 Hz, 1H), 5.72 (ddt, J=15.5, 5.7, 1.7 Hz, 1H), 4.76 (s, 4H), 4.58 (ddt, J=5.7, 1.4, 1.4 Hz, 1H), 3.99 (ddd, J=5.0, 1.6, 1.4 Hz, 2H), 3.63 (s, 3H), 3.21 (p, J=3.3, 1.6 Hz, 1H). $^{13}$C NMR (101 MHz, $CD_3OD$) δ 173.2, 132.2, 126.8, 70.9, 61.3, 51.2

EMBODIMENTS

1. A process for the preparation of alpha-hydroxy-beta-ene-acids or esters thereof of the formula

R'—HC═CH—CHOH—COOR  (I)

wherein
R is selected from the group consisting of —H and $C_1$-$C_8$-alkyl; and
R' is hydroxymethyl or 1,2-dihydroxyethyl;
the process comprising the steps of:
a. contacting a saccharide composition comprising one or more C6 and/or C5 saccharide units with a Lewis Acid material; and
b. recovering 2,5,6-trihydroxy-3-hexenoic acid and/or 2,5-dihydroxy-3-pentenoic acid or the esters thereof.

2. The process according to embodiment 1, wherein the esters of 2,5,6-trihydroxy-3-hexenoic acid or 2,5-dihydroxy-3-pentenoic acid are 2,5,6-trihydroxy-3-hexenoic acid methyl ester and 2,5-dihydroxy-3-pentenoic acid methyl ester.

3. The process according to any one of embodiments 1 or 2, wherein the saccharide composition comprises one or more C6 and/or C5 saccharide units selected from the group consisting of sucrose, xylose, mannose, tagatose, galactose, glucose, fructose, arabinose, inulin, amylopectin and sugar syrup.

4. The process according to any one of embodiments 1 to 3 wherein the saccharide composition contains at least 10% by weight of saccharide units.

5. The process according to any one of embodiments 1-4, wherein the saccharide composition comprises a polar solvent.

6. The process according to embodiment 5, wherein the saccharide composition comprises one or more solvents selected from the group consisting methanol, ethanol, DMSO and water.

7. The process according to any one of embodiments 1 to 6, wherein any alkali metal ion present in the saccharide composition is present in a concentration of less than 0.3 mM.

8. The process according to any one of embodiments 1 to 6, wherein the concentration of alkali metal ion in the saccharide composition is less than 0.3 mM.

9. The process according to any one of embodiments 1 to 8, wherein the Lewis acid material contains less than 0.5 wt % of alkali metal ion.

10. The process according to any one of embodiments 1 to 9, wherein the Lewis Acid material is Sn-BEA.

11. The process according to any one of embodiments 1 to 10, wherein the Lewis Acid material is Sn-MCM-41.

12. The process according to any one of embodiments 1 to 11, wherein the Lewis Acid material is tin salt, such as tin chloride (SnCl4 and SnCl2), tin fluoride (SnF4 and SnF2), tin bromide (SnBr4 and SnBr2), tin iodide (SnI4 and SnI2), tin acetylacetonate (SnC10H14O4), tin pyrophosphate (Sn2P2O7), tin acetate (Sn(CH3CO2)4 and Sn(CH3CO2)2), tin oxalate (Sn(C2O4)2 and SnC2O4), tin triflate ((CF3SO3)2Sn and (CF3SO3)4Sn)).

13. The process according to any one of embodiments 1 to 12, wherein the saccharide composition is contacted with the Lewis Acid material at a temperature of from 30 to 190° C.

14. The process according to embodiment 13, wherein the temperature is from 80 to 170° C.

15. The process according to any one of embodiments 1 to 14, wherein the saccharide composition is contacted with the Lewis Acid material for a period of at least 10 seconds.

16. The process according to any one of embodiments 1 to 15, wherein the process is conducted under continuous conditions.

17. The process according to embodiment 16, wherein the weight hourly space velocity is between 0.005 and 10 h$^{-1}$.

18. The process according to any one of embodiments 1 to 17, wherein the alpha-hydroxy-beta-ene-acids or esters thereof are subjected to a derivatization selected from acylation, silylation, alkylation, hydrolysis, hydrogenation, amidation.

19. The process according to any one of embodiments 1 to 18, wherein step b) includes a purification of the alpha-hydroxy-beta-ene-acids or esters or derivatives thereof.

20. The process according to embodiment 19 wherein the purification includes evaporating the solvent under reduced pressure.

21. The process according to any one of embodiments 19 or 20, wherein the purification includes purifying the alpha-hydroxy-beta-ene-acids or esters or derivatives thereof by column chromatography.

22. The process according to any one of embodiments 19 or 20, wherein the purification includes purifying the alpha-hydroxy-beta-ene-acids or esters or derivatives thereof by distillation.

23. The process according to any one of embodiments 19 or 20, wherein the purification includes purifying the alpha-hydroxy-beta-ene-acids or esters or derivatives thereof by crystallization.

The invention claimed is:

1. A process for the preparation of 2,5,6-trihydroxy-3-hexenoic acid and/or 2,5-dihydroxy-3-pentenoic acid or esters thereof of the formula

$$R'—HC=CH—CHOH—COOR \qquad (I)$$

wherein
R is selected from the group consisting of —H and $C_1$-$C_8$-alkyl; and
R' is hydroxymethyl or 1,2-dihydroxyethyl;
the process comprising the steps of:
a. contacting a saccharide composition comprising one or more C6 and/or C5 saccharide units with a Lewis Acid material; and
b. recovering 2,5,6-trihydroxy-3-hexenoic acid and/or 2,5-dihydroxy-3-pentenoic acid or the esters thereof,
wherein the Lewis Acid material comprises a framework structure and an active metal,
wherein the process results in a yield of 2,5,6-trihydroxy-3-hexenoic acid and/or 2,5-dihydroxy-3-pentenoic acid or esters thereof above 15%, and a yield of methyl lactate below 30%,
wherein a concentration of alkali metal ions present in an environment of the Lewis Acid material is kept at a concentration of less than 0.13 mM or at an amount of less than 0.5 wt % of a catalyst composition,
wherein the process is conducted under continuous conditions.

2. The process according to claim 1, wherein the esters of 2,5,6-trihydroxy-3-hexenoic acid or 2,5-dihydroxy-3-pentenoic acid are 2,5,6-trihydroxy-3-hexenoic acid methyl ester and 2,5-dihydroxy-3-pentenoic acid methyl ester.

3. The process according to claim 1, wherein the saccharide composition comprises one or more C6 and/or C5 saccharide units selected from the group consisting of sucrose, xylose, mannose, tagatose, galactose, glucose, fructose, arabinose, inulin, amylopectin and sugar syrup.

4. The process according to claim 1, wherein the saccharide composition contains at least 10% by weight of saccharide units.

5. The process according to claim 1, wherein the saccharide composition comprises a polar solvent.

6. The process according to claim 5, wherein the saccharide composition comprises one or more solvents selected from the group consisting methanol, ethanol, DMSO and water.

7. The process according to claim 1, wherein any alkali metal ion present in the saccharide composition is present in a concentration of less than 0.3 mM.

8. The process according to claim 1, wherein the Lewis acid material contains less than 0.5 wt % of alkali metal ion.

9. The process according to claim 1, wherein the Lewis Acid material is Sn-BEA.

10. The process according to claim 1, wherein the Lewis Acid material is Sn-MCM-41.

11. The process according to claim 1, wherein the saccharide composition is contacted with the Lewis Acid material at a temperature of from 30 to 190° C.

12. The process according to claim 11, wherein the temperature is from 80 to 170° C.

13. The process according to claim 1, wherein the saccharide composition is contacted with the Lewis Acid material for a period of at least 10 seconds.

14. The process according to claim 1, wherein the weight hourly space velocity is between 0.005 and 10 h$^{-1}$.

15. A process for the preparation of 2,5,6-trihydroxy-3-hexenoic acid and/or 2,5-dihydroxy-3-pentenoic acid or esters thereof of the formula

$$R'—HC=CH—CHOH—COOR \qquad (I)$$

wherein
R is selected from the group consisting of —H and $C_1$-$C_8$-alkyl; and
R' is hydroxymethyl or 1,2-dihydroxyethyl;
the process comprising the steps of:
a. contacting a saccharide composition comprising one or more C6 and/or C5 saccharide units with a Lewis Acid material; and
b. recovering 2,5,6-trihydroxy-3-hexenoic acid and/or 2,5-dihydroxy-3-pentenoic acid or the esters thereof,
wherein the Lewis Acid material comprises a framework structure and an active metal,
wherein the process results in a yield of 2,5,6-trihydroxy-3-hexenoic acid and/or 2,5-dihydroxy-3-pentenoic acid or esters thereof above 15%,
wherein a concentration of alkali metal ions present in an environment of the Lewis Acid material is kept at a concentration of less than 0.13 mM or at an amount of less than 0.5 wt % of a catalyst composition,
wherein the process is conducted under continuous conditions,
wherein the alpha-hydroxy-beta-ene-acids or esters thereof are subjected to a derivatization selected from acylation, silylation, alkylation, hydrolysis, hydrogenation, and amidation.

16. The process according to claim 1, wherein step b) includes a purification of the alpha-hydroxy-beta-ene-acids or esters thereof.

17. The process according to claim 1, wherein the concentration of alkali metal ions present in the environment of the Lewis Acid material is kept at a concentration of less than 0.13 mM.

18. A process for the preparation of alpha-hydroxy-beta-ene-acids or esters thereof of the formula

R'—HC=CH—CHOH—COOR    (I)

wherein
R is selected from the group consisting of —H and $C_1$-$C_8$-alkyl; and
R' is hydroxymethyl or 1,2-dihydroxyethyl;
the process comprising the steps of:
  a. contacting a saccharide composition comprising one or more C6 and/or C5 saccharide units with a Lewis Acid material; and
  b. recovering 2,5,6-trihydroxy-3-hexenoic acid and/or 2,5-dihydroxy-3-pentenoic acid or the esters thereof,
wherein the Lewis Acid material is a tin catalyst,
wherein the process results in a yield of alpha-hydroxy-beta-ene-acids or esters thereof above 15%, and a yield of methyl lactate below 30%,
wherein a concentration of alkali metal ions present in an environment of the Lewis Acid material is kept at a concentration of less than 0.13 mM or at an amount of less than 0.5 wt % of a catalyst composition,
wherein the process is conducted under continuous conditions.

19. A process for the preparation of 2,5,6-trihydroxy-3-hexenoic acid and/or 2,5-dihydroxy-3-pentenoic acid or esters thereof of the formula

R'—HC=CH—CHOH—COOR    (I)

wherein
R is selected from the group consisting of —H and $C_1$-$C_8$-alkyl; and
R' is hydroxymethyl or 1,2-dihydroxyethyl;
the process comprising the steps of:
  a. contacting a saccharide composition comprising one or more C6 and/or C5 saccharide units with a Lewis Acid material; and
  b. recovering 2,5,6-trihydroxy-3-hexenoic acid and/or 2,5-dihydroxy-3-pentenoic acid or the esters thereof,
wherein the Lewis Acid material is tin salt selected from the group consisting of tin chloride ($SnCl_4$ and $SnCl_2$), tin fluoride ($SnF_4$ and $SnF_2$), tin bromide ($SnBr_4$ and $SnBr_2$), tin iodide ($SnI_4$ and $SnI_2$), tin acetylacetonate ($SnC_{10}H_{14}O_4$), tin pyrophosphate ($Sn_2P_2O_7$), tin acetate ($Sn(CH_3CO_2)_4$ and $Sn(CH_3CO_2)_2$), tin oxalate ($Sn(C_2O_4)_2$ and $SnC_2O_4$), tin triflate (($CF_3SO_3)_2$ Sn and ($CF_3SO_3)_4$ Sn)) and mixtures thereof,
wherein the process results in a yield of 2,5,6-trihydroxy-3-hexenoic acid and/or 2,5-dihydroxy-3-pentenoic acid or esters thereof above 15%, and a yield of methyl lactate below 30%,
wherein a concentration of alkali metal ions present in an environment of the Lewis Acid material is kept at a concentration of less than 0.13 mM or at an amount of less than 0.5 wt % of a catalyst composition,
wherein the process is conducted under continuous conditions.

20. The process according to claim 19, wherein the alpha-hydroxy-beta-ene-acids or esters thereof are subjected to a derivatization selected from the group consisting of acylation, silylation, alkylation, hydrolysis, hydrogenation, and amidation.

* * * * *